US009022652B2

(12) United States Patent
Chupas et al.

(10) Patent No.: US 9,022,652 B2
(45) Date of Patent: May 5, 2015

(54) TRANSMISSION-GEOMETRY ELECTROCHEMICAL CELL FOR IN-SITU SCATTERING AND SPECTROSCOPY INVESTIGATIONS

(71) Applicants: Peter J. Chupas, Naperville, IL (US); Karena W. Chapman, Naperville, IL (US); Charles A. Kurtz, Bolingbrook, IL (US); Olaf J. Borkiewicz, Naperville, IL (US); Kamila Magdelena Wiaderek, Naperville, IL (US); Badri Shyam, Oak Park, IL (US)

(72) Inventors: Peter J. Chupas, Naperville, IL (US); Karena W. Chapman, Naperville, IL (US); Charles A. Kurtz, Bolingbrook, IL (US); Olaf J. Borkiewicz, Naperville, IL (US); Kamila Magdelena Wiaderek, Naperville, IL (US); Badri Shyam, Oak Park, IL (US)

(73) Assignee: UChicago Argonne, LLC, Chicgo, IL (US)

( * ) Notice: Subject to any disclaimer, the term of this patent is extended or adjusted under 35 U.S.C. 154(b) by 249 days.

(21) Appl. No.: 13/631,207

(22) Filed: Sep. 28, 2012

(65) Prior Publication Data
US 2014/0093052 A1  Apr. 3, 2014

(51) Int. Cl.
*G01N 23/00* (2006.01)
*G01N 23/20* (2006.01)
*H01M 10/48* (2006.01)

(52) U.S. Cl.
CPC .......... *G01N 23/20025* (2013.01); *H01M 10/48* (2013.01); *G01N 2223/307* (2013.01)

(58) Field of Classification Search
USPC ........... 378/44, 45, 46, 47, 53, 54, 70, 71, 73, 378/75, 79, 80, 81, 82, 83, 84, 86, 88, 89, 378/204, 208; 429/96, 99, 100
See application file for complete search history.

(56) References Cited

U.S. PATENT DOCUMENTS

| | | | |
|---|---|---|---|
| 5,253,280 A | 10/1993 | Mizuta | |
| 5,635,138 A | 6/1997 | Amatucci et al. | |
| 6,233,307 B1* | 5/2001 | Golenhofen | 378/45 |
| 7,022,290 B2 | 4/2006 | Gural et al. | |
| 7,729,471 B2* | 6/2010 | Burdett et al. | 378/47 |
| 2002/0179552 A1* | 12/2002 | Marraffa | 211/49.1 |
| 2002/0192121 A1* | 12/2002 | Gural et al. | 422/104 |
| 2011/0085638 A1* | 4/2011 | Kishida et al. | 378/45 |

OTHER PUBLICATIONS

Asakura et al., An Investigation of Electronic Structure of Novel Electrode Materials for Li-ion Batteries by Soft X-ray Absorption and Emission Spectroscopy II, Spring 2011, Activity Report, Institute for Solid State Physics, University of Tokyo, pp. 1, 2.*

(Continued)

*Primary Examiner* — David J Makiya
*Assistant Examiner* — Julio M Duarte-Carvajalin
(74) *Attorney, Agent, or Firm* — Cherskov Flaynik & Gurda, LLC

(57) ABSTRACT

The present invention relates to a test chamber that can be used to perform a variety of X-ray and neutron spectroscopy experiments including powder diffraction, small-angle scattering, X-ray absorption spectroscopy, and pair distribution functions, such chamber comprising a first electrode with an X-ray transparent window; a second electrode with an X-ray transparent window; a plurality of insulating gaskets providing a hermetic seal around the sample and preventing contact between said first and second electrodes; and an insulating housing into which the first electrode is secured.

18 Claims, 7 Drawing Sheets

(56) References Cited

OTHER PUBLICATIONS

Bertram et al., a compact high vacuum heating chamber for in-situ x-ray scattering studies, Aug. 2012, Rev. Sci. Instrum., vol. 83, pp. 2, 3.*

McDonald, small-angle x-ray scattering studies of nanostructured respirator and battery materials, Oct. 2013, MSc thesis, Dalhousie University, Halifax, Nova Scotia, pp. 12-20.*

* cited by examiner

TRANSMISSION-GEOMETRY ELECTROCHEMICAL CELL FOR IN-SITU SCATTERING AND SPECTROSCOPY INVESTIGATIONS

CONTRACTUAL ORIGIN OF THE INVENTION

The United States Government has rights in this invention pursuant to Contract No DE-AC02-06CH11357 between the United States Government and UChicago Argonne, LLC representing Argonne National Laboratory.

BACKGROUND OF THE INVENTION

1. Field of the Invention

The present invention relates to X-ray and neutron scattering experimentation devices, and more specifically, the present invention relates to an in-situ test chamber for an electrochemical cell.

2. Background of the Invention

X-ray and neutron scattering and spectroscopy techniques are common in many fields of science, especially those where the characterization of a micro- or nano-structured material is required.

There are a wide variety of X-ray scattering and spectroscopy techniques available to glean important information about a sample's structure. Spectroscopies and scattering methods are favored because they allow nondestructive testing of samples and inexpensive data collection compared to tunneling electron microscopes, scanning electron microscopes, or atomic probing. One of the greatest advantages of these methods is the ability to collect in-situ measurements, that is, measurements performed on the sample during actual use. Many other forms of scattering, spectroscopy and imaging require involved sample preparation or a high vacuum environment, which create unrealistic operating conditions for the sample.

X-ray scattering and spectroscopy involves bombarding samples with X-rays from an X-ray source such as a synchrotron. In some methodologies, a monochromator selects a particular X-ray wavelength, with other optical components focusing the beam before it hits the sample.

X-rays interact with electrons in a sample such that a variety of element specific and structural investigations can be performed. Structural investigations are of particular importance. By measuring the scattering angles of the secondary X-rays, crystallographic insights such as structure and other detail can be obtained. The scattering of X-rays is described by Bragg's law as follows:

$$n\lambda = 2d \sin \theta$$

where n is an integer corresponding to the number of X-ray wavelengths that fit between the lattice spacing, $\lambda$ is the wavelength of the incident X-ray, d is the spacing between the planes in the atomic lattice, and $\theta$ is the angle between the incident ray and the scattering plane. Because the wavelength of the incident X-ray is known and the scattering angle is detected, the lattice spacing can be found from the areas with a high concentration of reflections called Bragg peaks.

Several different X-ray characterization techniques are available, and each provides its own unique information. These techniques have been applied in the field of battery technology, but with limited results. As separate experimentation is required for each spectroscopic method, consistency of the sample is necessary to separate sample data from the background noise. This has proven to be the limiting step, and the problem is compounded by the variability introduced through the use of successive samples instead of a single one.

This is problematic as battery technology has become increasingly important in recent years, with the emphasis on green technologies, electric vehicles, and reducing dependence on foreign oil. For example, a need exists for batteries that can offer sustained voltages over their electrochemical cycle without experiencing tapering voltage as the cycle draws near completion and for batteries that are capable of long-term repeated cycling. Many of the most promising electrode/electrolyte combinations rely on intercalation of ions into the lattice structure of a larger crystal. In order for these reactions to take place, uniform nanostructured materials are needed. A means for characterizing nanostructured materials is currently lacking Battery technology can profit greatly from accurate nanostructure materials characterization. In order to get the maximum efficiency from electrode materials, the nanostructure changes in the electrode during the electrochemical cycle must be known. But, state of the art sample holders only allow battery components to be investigated over a single or, rarely, a second electrochemical cycle.

The most accurate way to determine the potential value of electrode materials is through in-situ experimentation, that is, during the electrochemical cycle of the battery. In-situ testing not only informs which materials have potential as electrodes but more importantly how they are able to operate effectively. Knowing why some materials work better than others can lead to a more directed and focused scientific inquiry. State-of-the-art ex-situ analysis fails to address this need. Typical ex-situ characterization techniques have several disadvantages: (1) they are extremely labor intensive because each cell requires disassembly to recover the electrode materials and each disassembly runs the risk of "short circuiting" the cell; (2) they require different samples to be studied at different points in the electrochemical cycle, so direct comparison of data is difficult; (3) in practice, ex situ techniques only allow a limited number of points in the cycle to be studied; and (4) they inhibit the investigation of highly-reactive, short-lived intermediaries because the delay involved in recovering the samples during disassembly of the testing device allows such intermediaries to decompose or react before the sample can be characterized.

Separately, currently available in-situ X-ray devices fail to perform the variety of measurements capable in the present invention.

State-of-the-art designs use flexible thin film windows, such as polyimide, aluminized Mylar, and "coffee bags," to transmit X-rays, which lead to inconsistent battery stack pressure. The flexibility of these materials creates a bulge over the center of the battery, causing a disparity in reaction rates between the center and outer regions of the battery where the stack pressure is maintained. Since the X-ray beam has a fixed height and width of a few hundred micrometers, the largest electrochemical deficiencies and least representative part of the sample coincides with the center of the window in the volume provided by the X-ray beam. Therefore, the area of the battery probed by the X-ray beam produces misleading and unrepresentative information about the reaction and structural changes.

Further, state of the art thin film windows can be permeable to ambient oxygen, nitrogen, and water, and these moieties react with many of the most promising battery components. Thus, the battery components deteriorate faster, limiting the number of possible cycles.

Conversely, rigid windows integrated with existing sample holder technologies allow for only limited data collection.

Such windows comprise beryllium substrates and electrode laminates deposited on foil current collectors. These are only compatible with a limited range of X-ray methodologies. The polycrystalline structure of these materials and the problematic elemental impurities create misleading scattering contributions, for example for pair distribution function (PDF) discussed infra.

A need exists in the art for a device and method to characterize battery electrodes in situ. The device and method should enable analysis via X-rays, including PDF characterization, and further facilitate electrochemical analysis. The device and method should also accommodate testing of full size batteries, a plurality of batteries, and battery stacks, all in real time.

SUMMARY OF INVENTION

An object of the invention is to provide a device and system for characterizing electrodes in situ that overcomes many of the drawbacks of the prior art.

Another object of the present invention is to provide a system for obtaining a variety of X-ray characterizations during electrochemical cycling of an experimental battery. A feature of the present invention is that a single sample positioned on a sample holder incorporated in the device can be used to perform several different X-ray characterizations. Another feature of the present invention is that the sample holding internal chamber (i.e., reaction cell) of the device utilizes wide-angle X-ray entrance and exit apertures. An advantage of the present invention is that the same sample can be used to collect data necessary for PDF measurements without the need for disassembling the sample.

Still another object of the present invention is to provide a device and method for collecting data in real-time during the electrochemical cycle of a cell. A feature of the present invention is the ability to continuously measure the reactivity of the cell while it is exposed to radiation such as X-rays. An advantage of the present invention is that a continuity of data points is collected because the cell is monitored continuously throughout its electrochemical cycle and during applications of different radiation sources.

Yet another object of the present invention is to reduce the time needed to make the micro- and nano-structure characterizations of an electrochemical cell. (Micro-characterizations deal with size ranges of between 100 microns and 0.1 microns and nano-characterizations deal with size ranges of between 100 nanometers and 0.1 nanometers.) A feature of the present invention is that a reaction cell containing the sample only need be assembled once. An advantage of the present invention is that short lived intermediaries of the cycle can be determined and analyzed in real time, without assembling, disassembling, and reassembling the reaction cell.

Another object of the present invention is to enable the continual, unbroken collection of data of reactions occurring in an electrochemical cell during substantially its entire discharge and charge cycles. A feature of the present invention is the ability to directly compare data collected at different points in electrochemical cycling of the same sample. Another feature is the ability to pause the cycling at any point and study the time-dependent evolution of any electrode components. An advantage of the present invention is that the reliability of data is greatly improved, which allows for more accurate structural information to be obtained.

Another object of the present invention is to provide a sample holder for characterizing an electrochemical cell, whereby the sample holder is designed to completely isolate the cell from the ambient environment in three assembly steps. Features of the present invention include few component pieces, guide pins to allow for quick alignment of the device's housing vis the cell, and direct screw tightening of the top electrode to the housing. An advantage of the present invention is that it reduces the risk of short-circuiting the cell during assembly or disassembly, which is a danger particularly relevant to lithium batteries.

Still another object of the present invention is to provide a method to accurately collect X-ray and electrical data during the electrochemical cycle of a cell. A feature of the present invention is the use of flexible, semi-rigid or rigid, electrically conductive, windows bonded to the electrode surfaces via conductive adhesive or other attachment means. An advantage of the present invention is that finer data points can be collected because the cell's electrical performance and electrode structure are monitored accurately throughout the electrochemical cycle. In instances where flexible windows are utilized, outgassing due to chemical reactions occurring within the cell are also monitored and analyzed.

Yet another object of the present invention is its ability to test a full "coin cell"-sized battery or a plurality of coin cell sized batteries. A feature of the present invention is a battery test chamber that substantially encapsulates components of a full size coin cell battery or a stack of such components to be tested. Another feature of the present invention is the ability to maintain exceptional electrical contact between the battery sample holder and the batteries themselves through the use of a screw tightening, snap fit, or friction fit assembly, electrically conductive windows, and variable gasket sizes and numbers. An advantage of the present invention is that realistic, real time working conditions for the battery are investigated while the battery or batteries are encapsulated within the sample holder.

In brief, the present invention provides a cell capable of in-situ wide-angle X-ray measurement and characterization utilizing semi-rigid or rigid radiation-transparent windows made from a glassy carbon and bonded to the electrodes surface using an electrically conductive epoxy. Rigid windows are defined as being windows made from a material that is hard to deform and experiences a minimal deformation when stack pressure is applied as opposed to non-rigid windows, which are flexible and deflect under stack pressure. In the primary embodiment of the invention, the cell is easy to assemble and permits the measurement of such X-ray methodologies as small angle X-ray scattering (SAXS), powder X-ray diffraction (pXRD), X-ray absorption spectroscopy (XAS), pair distribution functions (PDF) and similar investigations using neutron beams all in the same cell without multiple cell assemblies or disassemblies.

The present invention is a device for testing batteries with radiation, the device defining an axis and comprising a housing that comprises electrically conducting material; a first electrode adapted to be substantially received by the housing wherein the first electrode comprises a first surface defining a first aperture extending along the axis through the first electrode; an electrically conductive first radiation transparent window in electrical communication with said first surface, wherein the first window is adapted to be in electrical communication with a battery; a second electrode defining a second surface defining a second aperture extending through the second electrode said second aperture as to be coaxially aligned with the first aperture; a battery located on the axis in electrical communication with said first window; and a second electrically conductive radiation transparent window positioned between the second electrode and the battery so as to be in electrical communication with the second electrode and the battery.

BRIEF DESCRIPTION OF THE DRAWINGS

The invention together with the above and other objects and advantages will be best understood from the following detailed description of the preferred embodiment of the invention shown in the accompanying drawings, wherein.

DETAILED DESCRIPTION OF THE INVENTION

Figure 1:
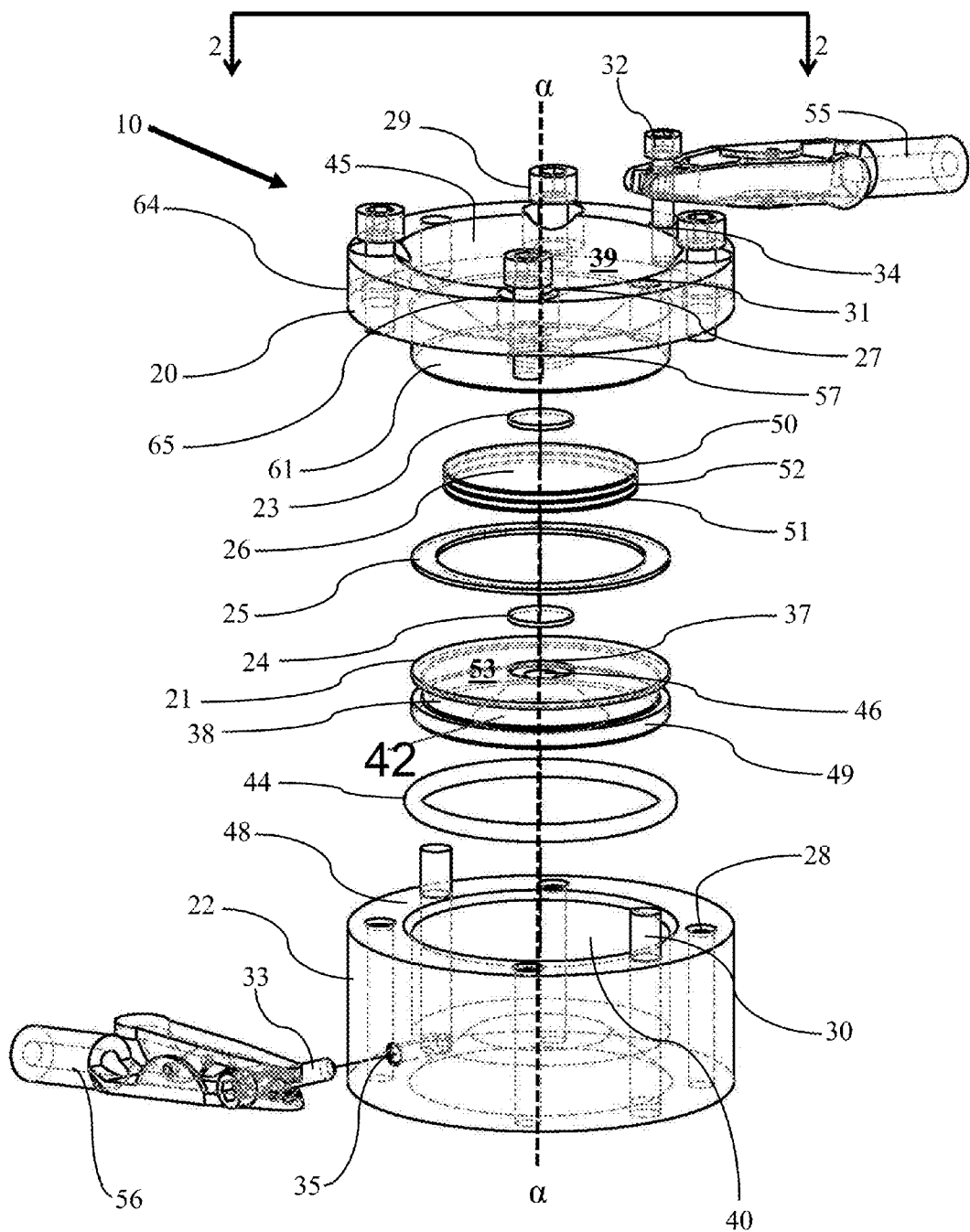
FIG. 1 depicts an exploded view of an embodiment of the invented test chamber for an electrochemical cell, in accordance with features of the present invention.

The foregoing summary, as well as the following detailed description of certain embodiments of the present invention, will be better understood when read in conjunction with the appended drawings. As used herein, an element or step recited in the singular and preceded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Battery technology continues to represent a major force in energy production, transport and storage. The inner workings of advanced batteries remain a mystery which must be solved to fully leverage this technology. For example, one of the most promising and widely researched fields of battery technology involves lithium intercalation batteries. Like all batteries, lithium batteries are made of an anode, cathode, and electrolyte. Typically the anode is graphite ($LiC_6$); the cathode is a metal oxide, such as lithium cobalt oxide ($LiCoO_2$) or lithium manganese oxide ($LiMn_2O_4$); and the electrolyte is a lithium salt in a non-aqueous organic solvent. During discharge, the lithium ions in the anode will insert themselves in the cathode, and during charging, the opposite takes place. When the lithium ions are inserted in either electrode, they place themselves in interstitial sites of the electrode lattice. Therefore, the ability to make precise crystallographic characterizations of electrode materials is a necessity. Finding electrode materials with structures that can more effectively accept and hold lithium ions will greatly improve the available charge storage, current, and reliability of these batteries.

The present invention provides a method and device to enable the aforementioned crystallographic characterizations. An embodiment of the present invention provides a cell capable of in-situ wide-angle X-ray measurement and characterization utilizing rigid X-ray transparent windows. In an embodiment of the invention, the windows comprise glassy carbon bonded to the electrodes' surface using an electrically conductive adhesive such as epoxy.

X-Ray Characterization
Technologies and Tools

In a preferred embodiment of the invention, the cell's basic design and relatively few components facilitate easy assembly and permits the use of such X-ray characterization tools as small angle X-ray scattering (SAXS), powder X-ray diffraction (pXRD), X-ray absorption spectroscopy (XAS), pair distribution functions (PDF) and similar investigations to map the changes in a sample's characteristics throughout many charge/discharge cycles without the need for multiple samples preparation.

Powder X-ray diffraction (pXRD) is a method of scattering that is useful for identifying crystalline materials by their structural characteristics. For example, a powder sample, comprised of particles varying in size from tens of nanometers to a few micrometers, is prepared so that every possible crystalline orientation is represented. The sample is bombarded with X-ray radiation, and the scattered radiation is detected. The resulting diffraction pattern displays Bragg peaks of high intensity that correspond to specific scattering angles. Because every crystalline material has a unique set of possible crystal structures and lattice spacings, the Bragg peaks obtained can be compared to known standards. This allows for easy confirmation of expected results or insight into the chemical mechanisms of unexpected results. However, the majority of the promising new electrodes cannot be characterized by pXRD due to the size of particles and amorphous nature of products of reaction.

Small angle X-ray scattering (SAXS) is a method of spectroscopy that can provide nanostructure detail. The technique involves shining a beam of X-ray radiation through a collimator onto a sample.

X-ray absorption spectroscopy (XAS) takes advantage of the dual nature of electrons as particles and waves. In XAS, the X-rays excite electrons to move between energy levels, and the resulting wave emissions are investigated. Because the emitted waves are scattered by surrounding atoms, distance between atoms can be determined based on the energy of the incident X-ray beam and the constructive and destructive amplification of the wave emission. The resulting wave patterns provide short range structural information about the object material as well as oxidation state of elements of interest Pair distribution function (PDF) analysis has emerged as a valuable tool for examining the local atomic structure of advanced materials. PDFs describe the distribution of distances between pairs of atoms in a given medium and have provided insight in the field of local structure analysis. However, PDFs are difficult to generate because of the precise total scattering data necessary to produce them. PDFs are the result of combined spectroscopy analysis. The insights from PDF can be compared to those from SAXS, pXRD, and XAS is combined.

As separate experimentation is required for each spectroscopic method, consistency of the sample is necessary to separate sample data from the background noise. Up until the advent of the instant device, consistency has been the limiting step, with the problem compounded by the variability introduced through the use of successive samples instead of a single one.

FIG. 1 depicts an exemplary embodiment of the invention in exploded view, designated as a reaction cell or sample holder, 10.

In the following description, a point of reference is taken relative to the radiation source (not shown) and the battery 26 residing in the chamber 10. As such, an "upstream" designation is generally indicative of regions of the device closest to the radiation source compared to "downstream designations. For a specific example, an upstream designation is where incoming radiation has yet to contact the battery 26. Conversely, a "downstream" designation is indicative of regions of the device downstream further away from the source of radiation.

As depicted in FIG. 1, the device is symmetrical around an axis α comprises a housing 22, a first or "top" electrode 20, and a second or "bottom" electrode 21. The first electrode 20 is adapted to be partially received by the housing 22, while the second electrode is adapted to be substantially entirely received by the housing. In an embodiment, the second electrode is completely encapsulated by the housing with no physical exposure to the environment. In an embodiment of the invention, the top and bottom electrodes and the housing are each machined from or molded with a single workpiece.

On an upstream side of the housing 22, the first electrode 20 defines a frustoconically shaped concave region 39, with a narrowest section terminating in an aperture 57 so as to be positioned downstream from a widest section located in the cantilevered portion 64; the second electrode 21 and housing 22 define a frustoconically shaped concave region 42 and 43, with a narrowest terminating in an aperture 46 upstream from a widest section at the farthest downstream portion of housing 22; with all frustoconically shaped concave regions coaxial with each other. Taken together, the housing, first electrode and second electrode, coaxially arranged, define an aperture through which X-rays pass. An axially symmetric frustoconical construction is easiest to properly align. In some instances this configuration allows greater flexibility in the choice of investigations carried out with the device but other arrangements can easily be inferred.

Positioned intermediate the first electrode 20 and the second electrode 21 is a battery 26 that is the object of study and which incoming X-rays, neutrons, or other radiation impinge, probe or otherwise contact.

Figure 2:
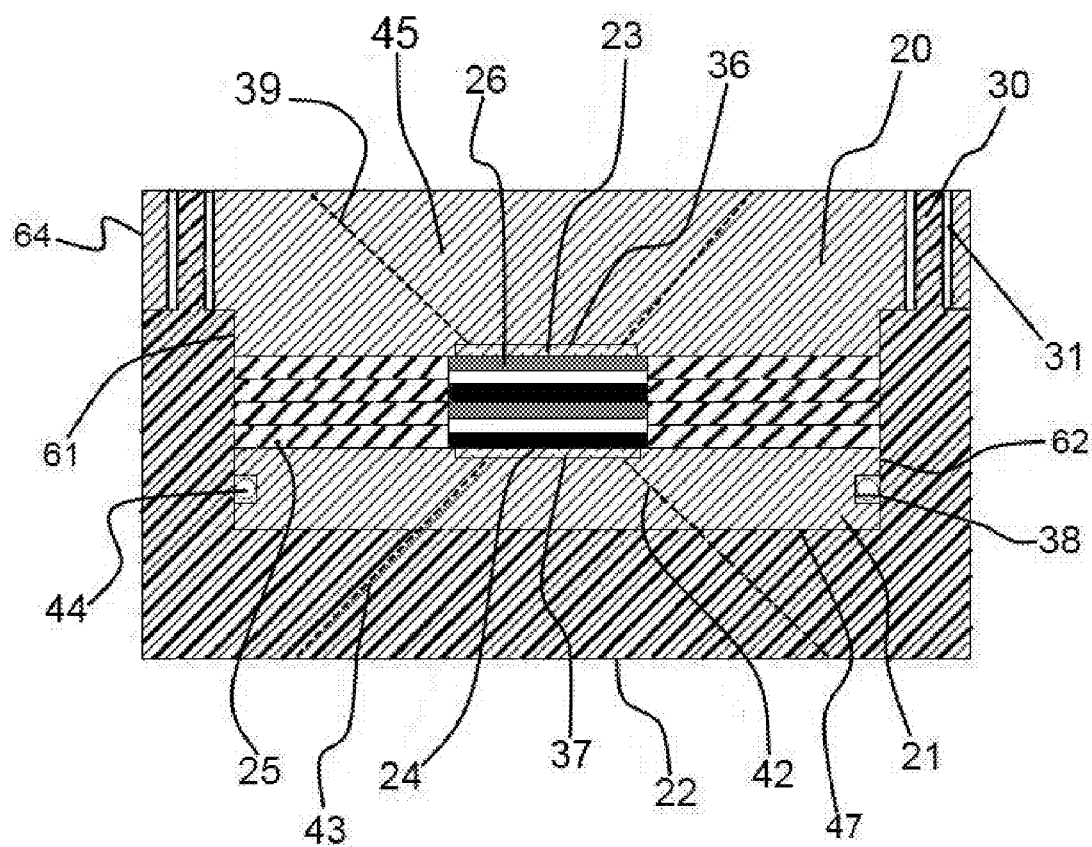
FIG. 2 depicts a cross-sectional view of the assembled test chamber taken along lines 2-2 of FIG. 1.

The housing 22 comprises insulating material while the electrodes comprise conducting material. This provides a means for electrically insulating the electrodes from each other. As shown in FIG. 2 the housing forms an open top void 45, defined by a medially facing surface 62 which is cylindrical and symmetric around the axis α. (For the sake of illustration the inside surface will be described as having as being a right circular cylinder but, other geometries are possible.)

The void further comprises a bottom surface 47 which is shown as planar in configuration but could be angular, concave, convex, or a myriad of other topographies. The bottom surface 47 is shown as orthogonal to the axis α, but a myriad of angles to the axis are suitable, and generally from 45-90 degrees. The open top void 45 defines a circumferentially extending rim 48 of the housing. Regions of the rim define longitudinally extending apertures such as threaded apertures 28 and adjacent longitudinally extending channels 31, the latter of which are adapted to receive guide pins 30. The threaded apertures 28 extend parallel to the axis α so as to provide a means for alignment and assembly of the cell components. The pins 30 fit into the guide pin holes 31 in the top electrode.

The bottom electrode 21 defines a substrate having a cross section slightly smaller than the inner diameter cross section of the housing 22. As such, the housing is adapted to slidably receive substantially the entirety of the second electrode 21. The second electrode 21 is shown shaped as a disk. As such, the disk's diameter is dimensioned to be less than the inner diameter of the cylindrical wall defining the cylinder shaped void 45 depicted in FIG. 2

The second or bottom electrode 21 further defines an axially extending concave frustoconical surface 42, such that the surface widens from the center (i.e. axis) of the electrode to a point on a depending surface of the electrode that is approximately midway between the center and the periphery of the second electrode 21. As such, the surface 42 faces away from the center of the housing interior (and therefore faces away from the battery, see FIG. 2) to provide an unhindered means of egress of the reflected x-rays emanating from the battery 26 and through the second electrode 21.

The housing also features a frustoconical surface 43 coaxial and continuous with the frustoconical surface 42 of the second electrode so as to facilitate unhindered egress of the reflected X-rays from the sample holder 10.

A medially (i.e. upstream) facing surface 53 of the second electrode opposes a downstream side of the battery. A region of the surface 53 coaxial with the axis of the chamber defines an aperture 46 to facilitate unhindered transmitted X-ray beam egress from the battery.

A conductive, and X-ray transparent window 24 covers the beam aperture 46. The window 24 is secured in a depression 37 depicted in FIG. 1 as contiguous with the periphery of the aperture 46. Depending on the depth of the depression, the window 24 may or may not be coplanar with the upstream facing surface 53 of the second electrode. For example, the window may be countersunk so as to nest within the aperture 46 and therefore below the upstream facing surface 53 of the second electrode. This example is a preferred embodiment when relatively thinner electrodes are utilized. In these instances the window is in electrical contact with the electrode only and the electrode is in contact with the battery.

However, a coplanar configuration is also preferred in many instances (empirically determined) as this provides for consistent stack pressure and optimizes electrical contact between the battery and electrodes. In these instances, both the electrode and the window are in physical contact with the battery.

A myriad of means can be used to secure the window within the depression, including reversibly attachment means such as spring clips, and permanent attachment means such as adhesive.

A myriad of means for removably positioning the second electrode at the downstream end of the chamber 10 exists. In one embodiment, as depicted, the laterally facing peripheral surface 49 of the second electrode defines a groove 38 adapted to receive an O-ring 44. Once this electrode/O-ring combination is established, the electrode is placed at the bottom of the chamber 10 so as to frictionally engage the interior wall surfaces of the housing 22.

The first (i.e. top) electrode 20 comprises two cylindrical regions: a central region 61 and a cantilevered region, 64, superior to, and overhanging the central region 61. The central region 61 is dimensioned so as to facilitate its nesting within the housing 22. An upstream surface of the first (i.e. top) electrode 20 defines a concave frustoconical surface, the center of which is coaxial to the axis of the chamber 10. The axial center of this surface defines an aperture 39 of a transversely extending tunnel through which radiation may traverse.

As described supra, the cantilevered region 64 overhangs the central region of the top electrode. Upon nesting of the first electrode 20 within the chamber, radially extending surfaces of the cantilevered region are positioned orthogonal to the axis α of the chamber 10. In this position, the longitudinally extending channels 31 formed along the periphery of the cantilevered region 64 of the first electrode 20 are in registration with the guide pins 30 and clearance cavities 65 on the rim 48 of the housing 22. Upon alignment, the first or top electrode 20 is joined to the housing via threaded bolts or screws 29, which mate with the threaded cavity 28. This relatively simple method of assembly allows for efficient setup and disassembly.

The device is assembled as follows: The bottom electrode 21 is slid into the housing 22 and placed in contact with the bottom or floor of the housing cup region 47. The rigid, electrically conductive X-ray transparent window 24 is placed over the aperture 46 and in a depression 37 of the bottom electrode. The battery stack 26 is placed on the surface 53 of the bottom electrode over the window 24. The battery is comprised of the components of an electrochemical cell, namely an anode 50, cathode 51, and an electrolyte separator 52. A gasket or plurality of gaskets 25 is then placed around the battery or battery stack 26. A plurality of gaskets may be used to adjust the height of the sample cavity to allow thicker batteries to be accommodated. Preferably, the initial gasket height should be greater than the height of the battery once the cell is assembled. Also preferably, the inner diameter of the gasket is greater than the diameter of the battery. The gasket provides a seal between the internal sample cavity, containing the battery stack, and the general atmosphere. Once the seal is formed, fluid/gas cannot be easily removed or squeezed from the cell. During assembly there is no air or moisture around the battery or cell as this is done within a controlled atmosphere argon filled glove box. The gasket physically isolates both the sample cavity from the plastic sample cup and isolates the two electrodes (and their respective windows) from each other. The height of the gasket or gaskets should be slightly higher than the height of the battery stack to account for the compression resulting from the attachment of the top electrode to the housing. (In instances where the second electrode is not outfitted with o-rings about its periphery, the number and thicknesses of the gaskets are also empirically determined depending on how much force is necessary to maintain the second electrode in place on the floor of the chamber.)

The top electrode 20 further contacts an electrically conductive X-ray transparent window 23 secured in the top electrode window depression 36. After the window is secured to the top electrode, the top electrode 20 is placed on gasket or gaskets 25 surrounding the battery 26. One or more screws 29 enter into cavities 65 in the top electrode 20 and are threadably mated with a corresponding threaded cavity 28 in the housing.

Gaskets 25 can be stacked to accommodate a larger (e.g. higher) battery stack 26, as can be seen in FIGS. 1 and 2. In these figures, the number of gaskets varies because the number of gaskets will depend on the thickness of the gasket material and the thickness of each battery cell. An important characteristic of this feature is that it provides a means for prohibiting moisture and air from entering the cell during characterization testing. In the embodiment shown, a hermetic seal is generated simultaneous with the generation of stack pressures. As the stack of gaskets is compressed via the screw tightening of the top electrode to the housing, the gaps between the gaskets allow for the egress of air. As the stack gets progressively more compressed, air is forced out through the gap between successive gaskets until the compression reaches the level where the rubber gaskets deform to the extent a gap between the successive gaskets no longer remains. In prior art designs, the seal is formed independently of stack pressure. Therefore, gases can be trapped within the test chamber, and the entrapped gases can resist compression. The entrapped gases distort the battery cell reaction through interaction with the battery components and prevent adequate stack pressure and the maintenance of electrical contact.

The test cell facilitates the measurement of reactivity during the electrochemical cycle of the sample battery 26. This is accomplished via an electrical conductor 33, which enters through a threaded connection hole 35 in the housing, and an electrical conductor 32, which is threadably mated with connection hole 34 in the top electrode. The electrical conductor 33 contacts the cylindrical wall 49 of the bottom electrode. Electrical leads 55 and 56 are connected to the conductors, and the leads are in turn connected to a load, which completes the cell circuit.

The electrical conductivity is aided by the use of, electrically conductive windows. Because the windows are rigid or semi-rigid, and electrically conductive, pressure from the top and bottom electrodes on the battery is maintained. This allows for increased electrical contact. If the pressure is not maintained, air gaps would be created in places where the component surfaces are not homogeneous. These air gaps prevent the flow of current in areas and contribute to inaccurate measurements of cell capability. State-of-the-art soft windows cause losses in stack pressure and therefore decreased electrical contact.

Further aiding the electrical conductivity are the frustoconical apertures. The center of the aperture is substantially coaxial with the longitudinal axis α of the chamber 10, and therefore centered over the battery or battery stack. Thus, the inner portion of the battery contacts the rigid window covering the aperture and the outer portion of the battery is in contact with the metal electrode.

As can be seen in FIG. 2, the frustoconical aperture allows for the flat, inner surface on the electrode to contact a large surface area of the battery, providing the electrical path necessary to complete the circuit. The aperture also provides an opening at the outer surfaces to allow scattered and transmitted X-rays to be detected.

Figure 3:
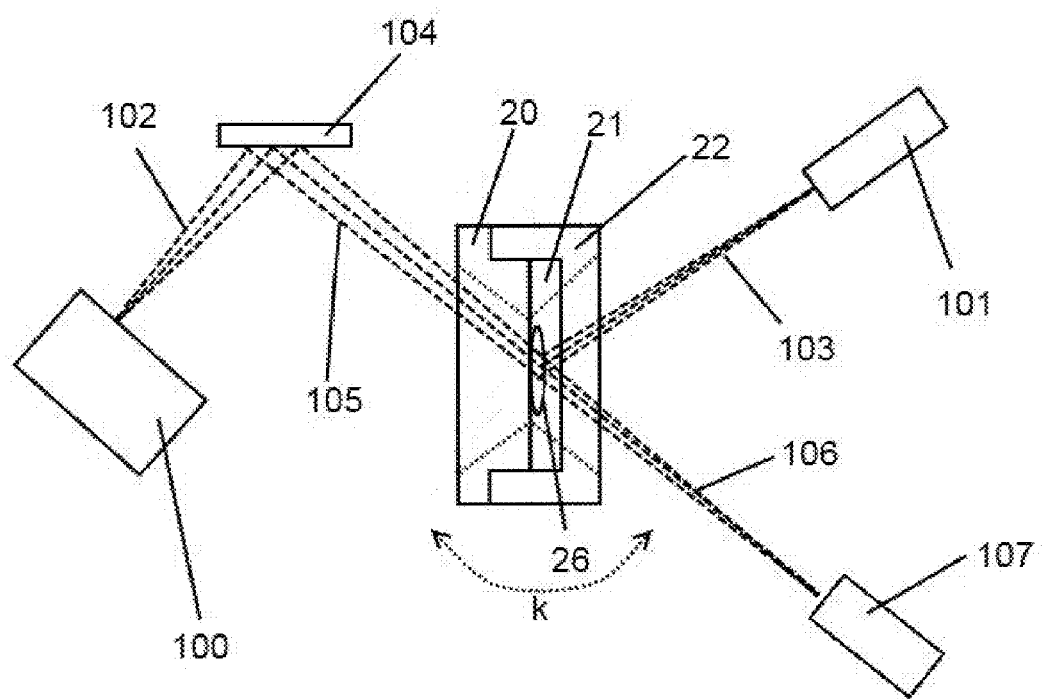
FIG. 3 depicts the Debye-Scherrer geometry utilized in battery characterizations, in accordance with features of the present invention.

X-ray characterization of the battery can begin when the electrochemical cycle is in process. FIG. 3 shows the Debye-Scherrer geometry, which is the transmission geometry. In FIG. 3, an X-ray source 100 reflects the beam 102 off of a monochromator 104. The monochromated beam 105 then irradiates the sample, which is moved along arc k. The transmitted beam 106 terminates at the beam stop 107. The diffracted beam 103 is captured by the detector 101. In the studies relevant to the field of batteries, transmission geometry is the most desirable and appropriate for the study.

The invention's ability to capture data continuously (e.g., in real time) results in a data density that is 20 to 100 times greater than that gleaned from ex-situ studies of recovered materials. Data intervals generated in real time maximize analysis of more complex materials and reactions. For example, any short-lived intermediates are detected and identified using the invented device and method.

In construction of the test electrochemical cell, the following materials were found to perform satisfactorily. Stainless steel 316 was chosen for the top and bottom electrodes because of its low chemical reactivity and low electrical impedance. Polycarbonate resin was selected for the housing because of the outstanding mechanical strength and the electrical insulation of battery stack components. The X-ray transparent windows are comprised of materials commercially available. Suitable materials include glassy carbon, Ni-plated glass, diamond, and Ni-plated plymers, all of which are commercially available. For example, a commercially available glassy carbon substrate is Sigradur G™, manufactured by HTW Hochtemperatur-Werkstoffe GmbH, Thierhaupten Germany. The windows are bonded to the electrode surfaces using an electrically conductive adhesive such as epoxy. Lastly, the gaskets are comprised of electrically nonconductive, reversibly deformable material. In embodiment, gaskets were cut from 0.79 mm (1/32" inch) fluorsilicone rubber sheets.

Figure 4A:
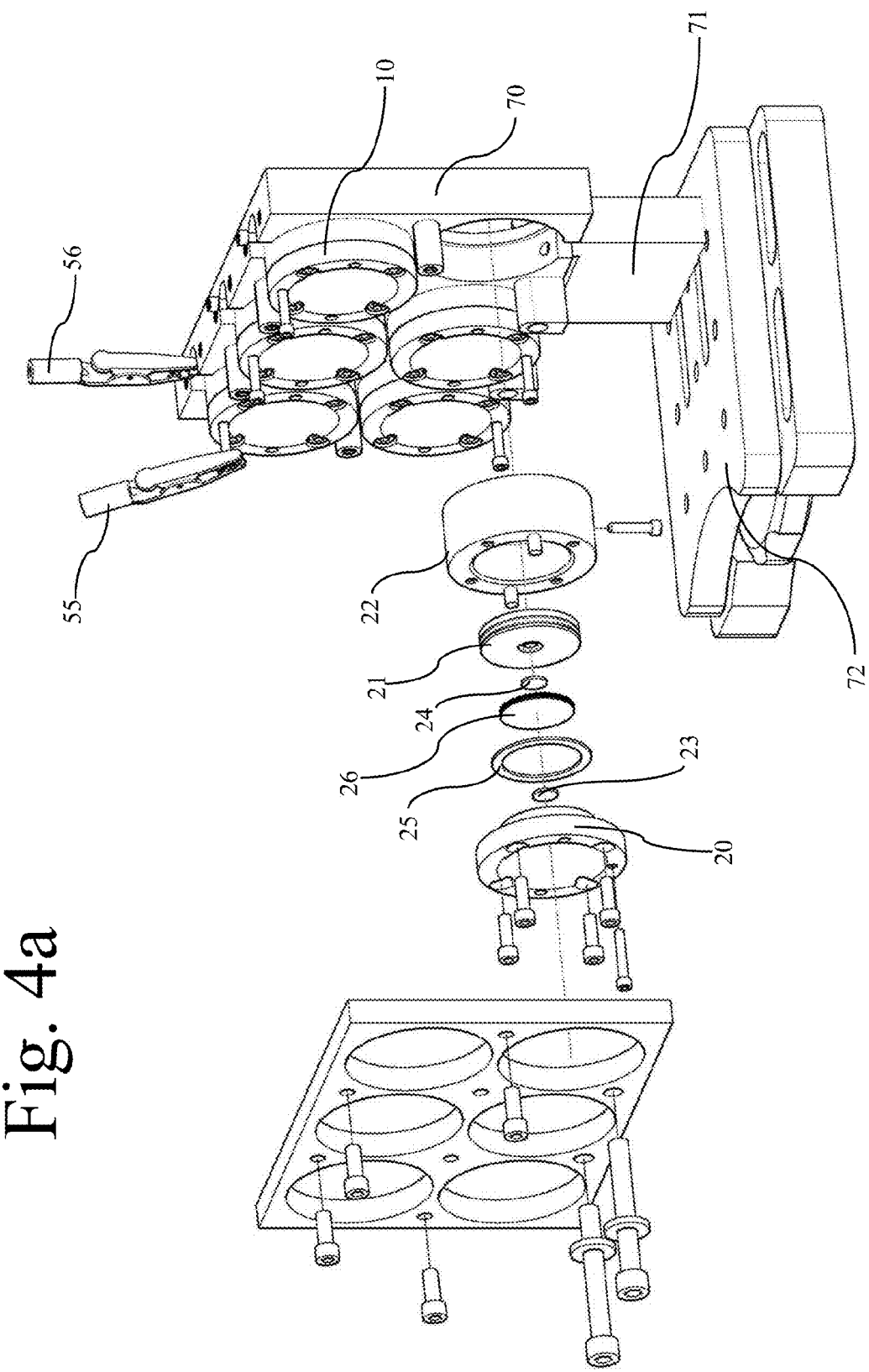
FIG. 4A is an exploded front view of a device for performing multiple experiments using a plurality of sample holders, in accordance with features of the present invention.
Figure 4B:
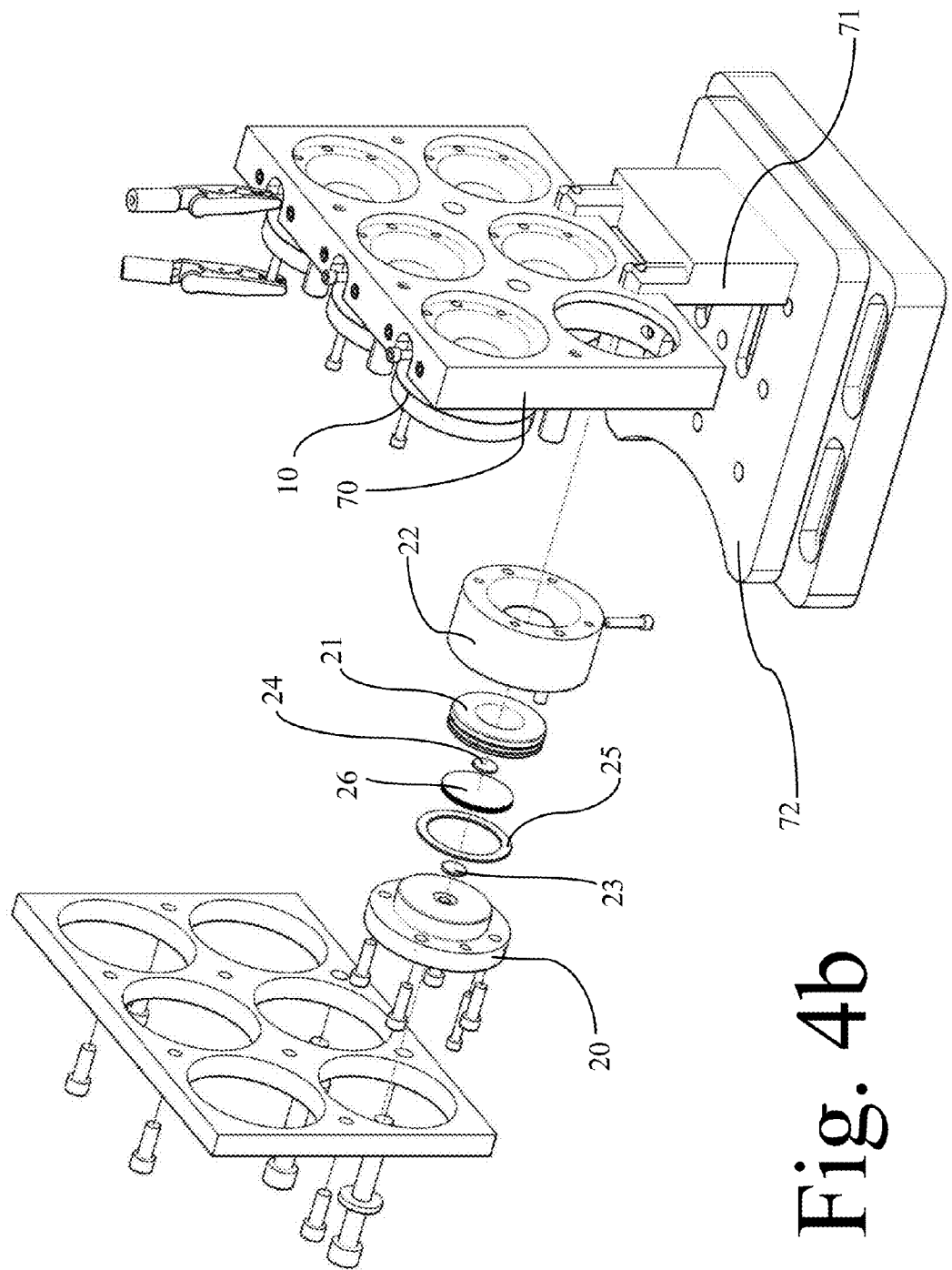
FIG. 4B is an exploded back view of a device for performing multiple experiments on a plurality of cells contained in a plurality of sample holders, in accordance with features of the present invention.

X-ray characterizations can be undertaken on a multitude of batteries at the same time as can be seen in FIG. 4. The sample holder 10 is secured in an array 70 with the first, or top, electrode 20 facing the incident beam. The incident beam irradiates each cell one at a time, traveling through transparent window 24 in aperture 46. The array 70 is supported by a stand 71, which is mounted in a base 72. The array holder 70 may contain heating elements to investigate temperature dependences or to increase the rate of reaction kinetics. The use of heating tape can provide the heat source. The heating tape is wrapped around the portion of the individual cells that projects from the array. A single heat-resistant plastic shield with a number of holes equal to the number of cells in the array and large enough to accommodate the cells wrapped in heating tape secures the heating tape around the cells. The array holder 70 may also contain a source of flowing inert gas to prevent the corrosion of the X-ray transparent windows 23 and 24 when particularly corrosive electrolytes are present. The inert gas is piped in through a valve-capped hole in the array. A polyamide sheet is wrapped around the array in such a way as to provide a seal on three of the array sides, including the side containing the inert gas valve. No seal is maintained on the side opposite the valve so as to provide a means of egress for the flowing gas. The cell holder pictured in FIG. 4 accommodates six cells, but arrays that accommodate lesser or greater numbers of cells are easily envisioned. Aluminum was found to be a suitable material for construction of the array 70 because of its exceptional heat conductivity.

Figure 5A:
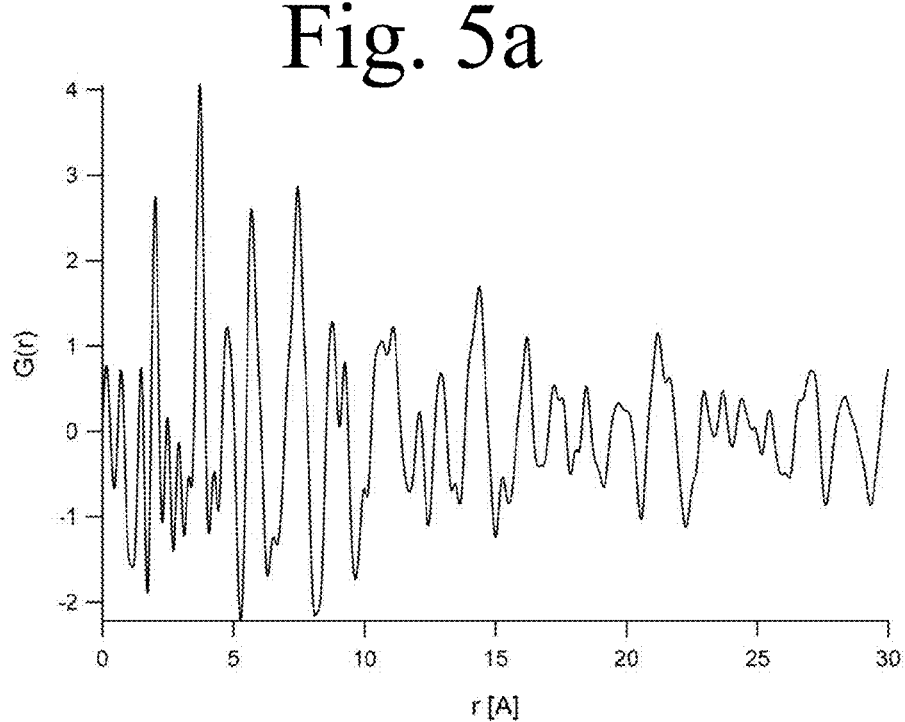
FIG. 5A is a PDF function generated by the invented device in operation.

FIG. 5A shows a single Pair Distribution Function (PDF) generated by in-situ testing with the test chamber. As stated above, PDFs provide a great deal of information about the structural changes that a battery undergoes during the electrochemical cycle. The peak position provides information about atomic distances. The peak area provides bonding information such as the coordination number. The width of a peak describes the relative order or disorder in the structure. The largest distance at which well-defined features are observed provides an estimate of the average particle size or ordered region.

Figure 5B:
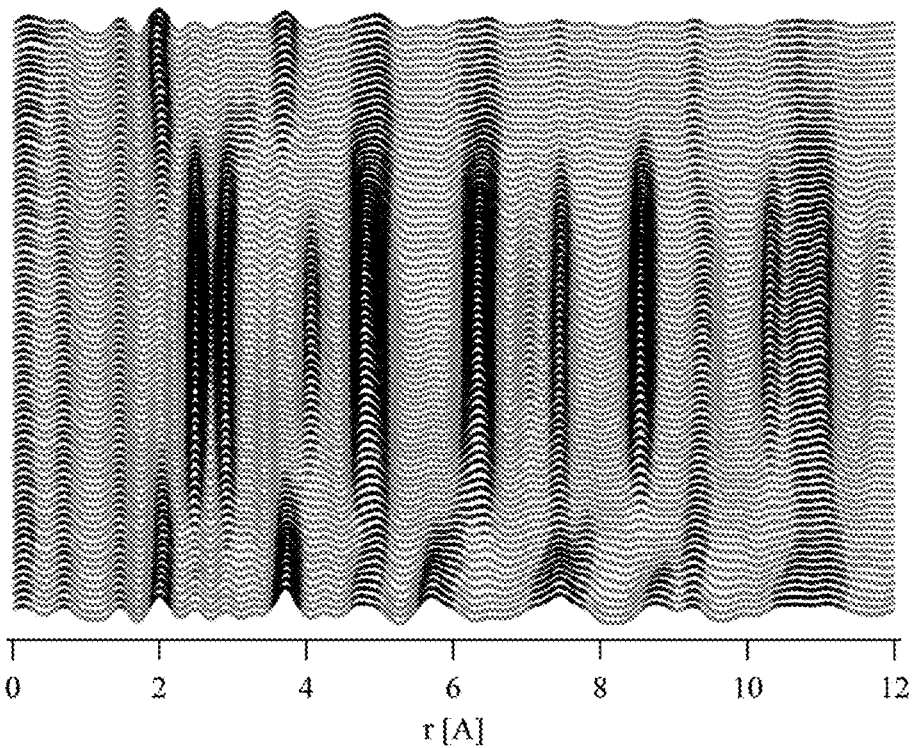
FIG. 5B is a series of PDF functions generated by the invented device in operation.

Further, the average particle size can be discerned. FIG. 5B shows a top view of a series of PDFs generated every one half-hour through in-situ testing. By tracking the movement of peaks, the structural changes that the materials undergo during electrochemical cycling can be observed. This provides valuable insight into the chemical mechanisms of the reaction and can direct further research into similar materials. The interval times represented in FIG. 5B are not meant to suggest a limitation of the device. Shorter interval times are accommodated by the test chamber but are not generally necessary for observation purposes.

The present invention can readily be adapted to allow the testing of a fuel cell instead of the battery 26. All one need do is provide conduits for fluid supply and egress at the location of the battery 26. These conduits also facilitate the analysis of the electrochemistry via wet bench or chromatographic means.

Figure 6A:
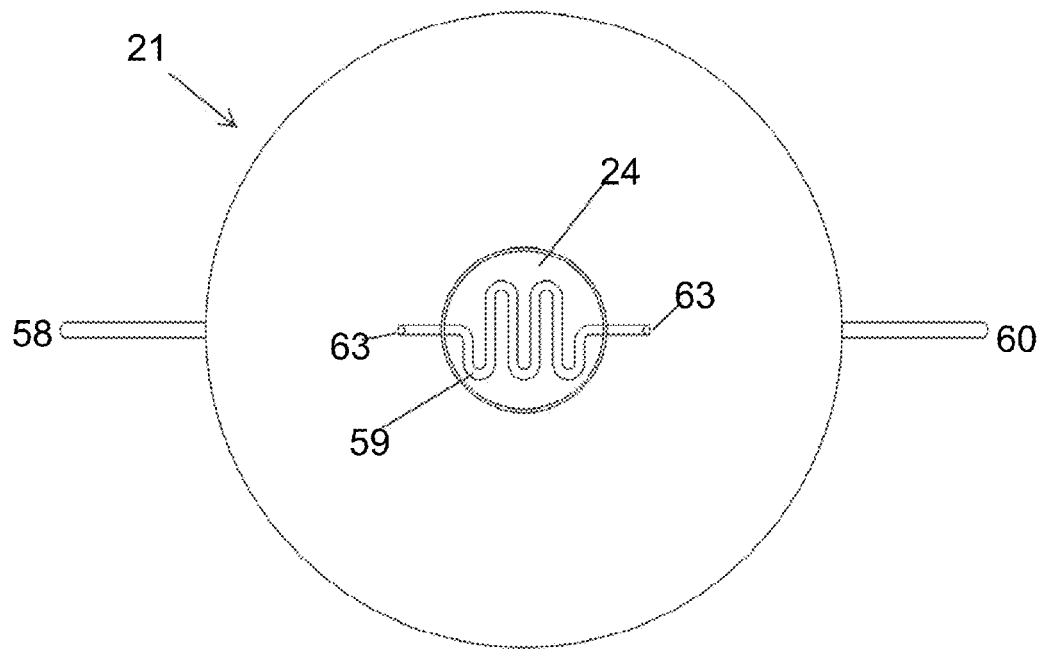
FIGS. 6A and B are plan and perspective views of a portion of the invented device for accommodating testing of fuel cells, in accordance with features of the present invention.
Figure 6B:
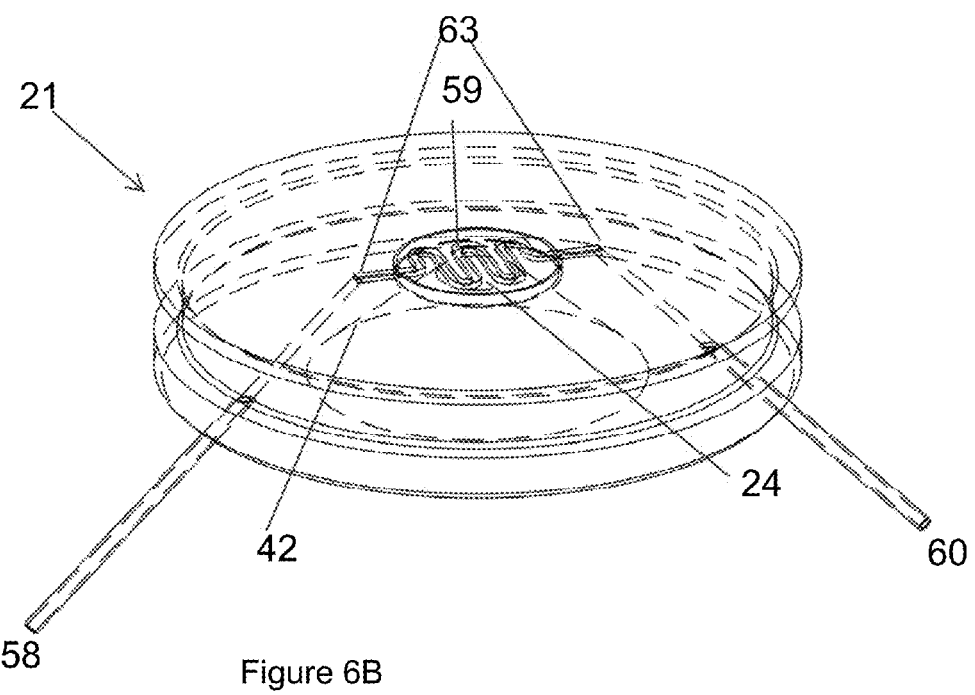

FIGS. 6A and B depict a bottom electrode 21 for incorporation in the invented test cell when fuel cells are to be characterized. FIG. 6A is a plan view of the bottom electrode while FIG. 6B is a perspective view of the bottom electrode 21. A means of fluid ingress 58 and egress 60 from the test cell is provided to facilitate transport of reactive moieties to and from the internal spaces of the test cell. These ingress and egress means terminate at a point exterior from the electrode 21 and preferably at a point exterior of the testing cell 10.

The upwardly facing surface of the bottom electrode window 24 of this fuel cell characterization configuration defines a fluid trough 59 cut, carved or etched into it. This trough is configured to maximize fluid communication to a fuel cell it is in contact with, said fuel cell positioned where the battery 26 is positioned in the battery testing device. This allows the fuel cell to physically contact the open top of the trough to establish fluid communication between the trough and the fuel cell. FIG. 6 depicts a serpentine configuration to the path, but other configurations are also suitable. For example, a plurality of troughs can be etched into the window to maximize fluid communication with the overlaying fuel cell.

The ends of the trough terminate beyond the periphery of the window as conduits 63 such as closed top tubes or pipes. These conduits 63 are in fluid communication with the fluid ingress-58 and egress-60 means.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. For example, the invented device can be fitted with optional flexible (e.g., non-rigid or semi-rigid) windows. This provides a means for evaluating and mapping the pressure dependence of the electrochemical reaction in a battery electrode. The flexible window provides a distribution of force on the battery material over the window area. By directing the X-ray beam through various different areas of the window and probing the condition of the battery at each of these points, this enables mapping the dependence of the electrochemical reaction on stack pressure and identifying electrode materials that tolerate a wide range of pressures. Mounting of the flexible window is similar to that of rigid or semi-rigid mounting detail described supra. Preferably, the flexible windows are electrically conductive and air and moisture impermeable.

While the dimensions and types of materials described herein are intended to define the parameters of the invention, they are by no means limiting, but are instead exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

The present methods can involve any or all of the steps or conditions discussed above in various combinations, as desired. Accordingly, it will be readily apparent to the skilled artisan that in some of the disclosed methods certain steps can be deleted or additional steps performed without affecting the viability of the methods.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

The embodiment of the invention in which an exclusive property or privilege is claimed is defined as follows:

1. A device for testing one or more batteries with electromagnetic radiation between the wavelengths of $10^{-10}$ and $10^{-5}$ m or neutron radiation, the device defining an axis and comprising:
    a housing that comprises electrically insulating material;
    a first electrode adapted to be substantially received by the housing wherein the first electrode comprises a first surface defining a first frustoconical aperture extending along the axis through the first electrode;
    an electrically conductive first radiation transparent window in electrical communication with said first surface, wherein the first window is adapted to be in electrical communication with a battery and wherein the first window is transparent to electromagnetic radiation between the wavelengths of $10^{-10}$ and $10^{-5}$ m or neutrons;
    a second electrode defining a second surface defining a second frustoconical aperture extending through the second electrode said second aperture being coaxially aligned with the first aperture;
    a battery located on the axis in electrical communication with said first window;
    a second electrically conductive radiation transparent window positioned between the second electrode and the battery so as to be in electrical communication with the second electrode and the battery, wherein the second window is transparent to electromagnetic radiation between the wavelengths of $10^{-10}$ and $10^{-5}$ m or neutron.

2. The device as recited in claim 1 further comprising a plurality of insulating gaskets providing a hermetic seal around the batteries and preventing contact between said first and second electrodes.

3. The device as recited in claim 1 further comprising conductive epoxy seals between said electrodes and said windows.

4. The device as recited in claim 1 comprising a plurality of fastening means received by bores in said housing and allowing compression of the batteries between said electrodes.

5. The device of claim 1 in which the frustoconical apertures have apex angles that extend up to 110 degrees.

6. A sample holder for in-situ radiation characterization of a sample in a cell, the holder comprising:
    a first electrode with an X-ray transparent window attached thereto and with a frustoconical aperture radially extending from the periphery of said window of said first electrode to an outer surface of said first electrode;
    a second electrode with an X-ray transparent window attached thereto and with a frustoconical aperture radially extending from the periphery of said window of said second electrode to the outer surface of said second electrode;
    at least one gasket, surrounding the sample and located between said first and second electrode, which is sufficient to provide a hermetic seal and which is sufficient to prevent electrical communication between said first and second electrodes; and
    an electrically insulating housing that contains said second electrode and that allows for compression of the cell via a fastening mechanism with the first electrode.

7. The sample holder of claim 6 in which apex angles of said frustoconical apertures extend up to 110 degrees.

8. The sample holder of claim 6 in which said windows provide constant pressure on the sample of characterization.

9. The sample holder of claim 6 in which said windows are electrically conductive.

10. The sample holder of claim 6 in which said windows comprise glassy carbon.

11. The sample holder of claim 6 in which said first and second electrodes, said one or more gaskets, and said electrically insulating housing are designed to accommodate the components of a full size coin cell battery.

12. The sample holder of claim 6 in which said windows are in electrical contact with the electrodes to which the windows are attached.

13. An array of cells for in-situ radiation characterization of batteries using electromagnetic radiation between the wavelengths of $10^{-10}$ and $10^{-5}$ m or neutron radiation, the array comprised of:
    a plurality of individual cells with each cell being comprised of:
        a first electrode with a radiation transparent window and with a frustoconical cavity radially extending from the periphery of said window of said first electrode to the outer surface of said first electrode, wherein the window of said first electrode is transparent to electromagnetic radiation between the wavelengths of $10^{-10}$ and $10^{-5}$ m or neutron radiation;
        a second electrode with a radiation transparent window and with a frustoconical cavity radially extending from the periphery of said window of said second electrode to the outer surface of said second electrode, wherein the window of said second electrode is transparent to electromagnetic radiation between the wavelengths of $10^{-10}$ and $10^{-5}$ m or neutron radiation; and
        at least one insulating gasket surrounding an object of radiation characterization using electromagnetic radiation between the wavelengths of $10^{-10}$ and $10^{-5}$ m or neutron radiation and located between said first and second electrodes sufficient to provide a hermetic seal and sufficient to prevent electrical communication between said first and second electrodes an array substrate designed to hold said plurality of cells; and a stand designed to align said array substrate in an orientation to receive incident electromagnetic radiation between the wavelengths of $10^{-10}$ and $10^{-5}$ m or neutron radiation.

14. The array of cells of claim 13 in which said array substrate contains a heating element in contact with at least one of said individual cells.

15. The array of cells of claim 13 in which said array substrate provides an inert atmosphere across said windows to prevent degradation of the windows by corrosive objects.

16. The array of cells as recited in claim 13 wherein the windows are rigid.

17. The array of cells as recited in claim 13 wherein the windows are flexible.

18. The array of cells as recited in claim 13 wherein the array is adapted to be enclosed in a controlled environment.

\* \* \* \* \*